US011206976B2

(12) United States Patent
Smith

(10) Patent No.: US 11,206,976 B2
(45) Date of Patent: Dec. 28, 2021

(54) METHOD AND SYSTEM FOR SIMULTANEOUS DECOMPOSITION OF MULTIPLE HYPERSPECTRAL DATASETS AND SIGNAL RECOVERY OF UNKNOWN FLUOROPHORES IN A BIOCHEMICAL SYSTEM

(71) Applicant: New York University, New York, NY (US)

(72) Inventor: R. Theodore Smith, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 1123 days.

(21) Appl. No.: 14/884,445

(22) Filed: Oct. 15, 2015

(65) Prior Publication Data

US 2016/0106311 A1 Apr. 21, 2016

Related U.S. Application Data

(60) Provisional application No. 62/064,851, filed on Oct. 16, 2014.

(51) Int. Cl.

| | |
|---|---|
| G01N 33/48 | (2006.01) |
| A61B 3/00 | (2006.01) |
| A61B 3/14 | (2006.01) |
| A61B 3/12 | (2006.01) |
| A61B 3/10 | (2006.01) |
| G01J 3/44 | (2006.01) |
| G01N 21/64 | (2006.01) |
| G16H 50/20 | (2018.01) |
| G16B 40/10 | (2019.01) |
| G16H 30/00 | (2018.01) |

(52) U.S. Cl.
CPC .............. *A61B 3/0025* (2013.01); *A61B 3/10* (2013.01); *A61B 3/1025* (2013.01); *A61B 3/12* (2013.01); *A61B 3/14* (2013.01); *G01J 3/4406* (2013.01); *G01N 21/6486* (2013.01); *G16B 40/10* (2019.02); *G16H 30/00* (2018.01); *G16H 50/20* (2018.01); *G01N 2021/6417* (2013.01)

(58) Field of Classification Search
None
See application file for complete search history.

(56) References Cited

U.S. PATENT DOCUMENTS

| | | | | |
|---|---|---|---|---|
| 9,622,662 | B2* | 4/2017 | Zuzak | ................ A61B 5/14551 |
| 2014/0105918 | A1* | 4/2014 | Gomis | ................ C12Q 1/6886 |
| | | | | 424/174.1 |
| 2015/0294458 | A1* | 10/2015 | Biernat | ................ A61B 3/0058 |
| | | | | 382/131 |

OTHER PUBLICATIONS

Vaclavik, Veronika, et al. "Autofluorescence imaging in age-related macular degeneration complicated by choroidal neovascularization: a prospective study." Ophthalmology 115.2 (2008): 342-346.*
Lee et al., "In vivo snapshot hyperspectral image analysis of age-related macular degeneration", Engineering in Medicine and Biology Society (EMBC), Sep. 2010, pp. 5363-5366.
Sajda, "Machine learning for detection and diagnosis of disease," Annu. Rev. Biomed. Eng., vol. 8, Apr. 2006, pp. 537-565.
Sajda et al., "Nonnegative matrix factorization for rapid recovery of constituent spectra in magnetic resonance chemical shift imaging of the brain", IEEE Trans. Med. Imaging, vol. 23, No. 12, Dec. 2004, pp. 1453-1465.
Sajda et al., "Recovery of constituent spectra using non-negative matrix factorization", Proceedings of SPIE, vol. 5207, 2003, pp. 321-331.
Curcio et al., "Structure, function, and pathology of Bruch's membrane", Retina, Fifth ed., 2013, pp. 465-481.
Shashua et al., "Non-negative tensor factorization with applications to statistics and computer vision", Proceedings of the 22nd International Conference on Machine Learning, 2005, pp. 792-799.
Neher et al., "Blind source separation techniques for the decomposition of multiply labeled fluorescence images", Biophys. J., vol. 96, No. 9, May 2009, pp. 3791-3800.
Cichocki et al., "Nonnegative Matrix and Tensor Factorizations: Applications to Exploratory Multi-Way Data Analysis and Blind Source Separation", John Wiley & Sons, 2009, 205 sheets.
Sparrow et al., "The bisretinoids of retinal pigment epithelium", Prog. Retin. Eye Res., vol. 31, No. 2, Dec. 2012, pp. 121-135.
Strauss, "The retinal pigment epithelium in visual function", Physiol. Rev., vol. 85, No. 3, 2005, pp. 845-881.
Ts'o et al., "The retinal pigment epithelium: I. Comparative histology", Arch. Ophthalmol., vol. 78, No. 5, 1967, pp. 641-649.
Sparrow et al., "Phospholipid meets all-trans-retinal: the making of RPE bisretinoids", J. Lipid Res., vol. 51, No. 2, Aug. 2010, pp. 247-261.
Feeney, "Lipofuscin and melanin of human retinal pigment epithelium. Fluorescence, enzyme cytochemical, and ultrastructural studies", Invest. Ophthalmol. Vis. Sci., vol. 17, No. 7, 1978, pp. 583-600.
Ng et al., "Retinal pigment epithelium lipofuscin proteomics", Mol. Cell. Proteomics, vol. 7, No. 7, Apr. 2008, pp. 1397-1405.
Tang et al., "New insights into retinoid metabolism and cycling within the retina", Prog. Retin. Eye Res., vol. 32, Oct. 2013, pp. 48-63.
Hwang et al., "Predictive value of fundus autofluorescence for development of geographic atrophy in age-related macular degeneration", Invest. Ophthalmol. Vis. Sci., vol. 47, No. 6, Jun. 2006, pp. 2655-2661.

(Continued)

*Primary Examiner* — Anna Skibinsky
(74) *Attorney, Agent, or Firm* — Fay Kaplun & Marcin, LLP

(57) ABSTRACT

A system and method are for analyzing fluorescence of fluorophors in an eye using a non-negative matrix factorization (NMF) method. The NMF method may be initialized with Gaussian mixture model fits and may optionally be constrained to provide identical abundance images for data obtained in response to two or more excitation wavelengths.

8 Claims, 12 Drawing Sheets

(56) References Cited

OTHER PUBLICATIONS

Eldred et al., "Fluorophores of the human retinal pigment epithelium: separation and spectral characterization", Exp. Eye. Res., vol. 47, No. 1, Aug. 1988, pp. 71-86.

Ablonczy et al., "Lack of correlation between the spatial distribution of A2E and lipofuscin fluorescence in the human retinal pigment epithelium", Invest. Ophthalmol. Vis. Sci., vol. 54, No. 8, Apr. 2013, pp. 5535-5542.

Sparrow et al., "Experimental approaches to the study of A2E, a bisretinoid lipofuscin chromophore of retinal pigment epithelium", Methods Mol. Bio., vol. 652, 2010, pp. 315-327.

Kim et al., "The all-trans-retinal dimer series of lipofuscin pigments in retinal pigment epithelial cells in a recessive Stargardt disease model", Proc. Natl. Acad. Sci. U. S. A., vol. 104, No. 49, Oct. 2007, pp. 19273-19278.

Wu et al., "Novel lipofuscin bisretinoids prominent in human retina and in a model of recessive Stargardt disease", J. Biol. Chem., vol. 284, No. 30, Jul. 2009, pp. 20155-20166.

Yamamoto et al., "A novel bisretinoid of retina is an adduct on glycerophosphoethanolamine". Invest. Ophthalmol. Vis. Sci., vol. 52, No. 12, Oct. 2011, pp. 9084-9090.

Ablonczy et al., "The utilization of fluorescence to identify the components of lipofuscin by imaging mass spectrometry", Proteomics, vol. 14, No. 7-8, Dec. 2014, pp. 936-944.

Weiter et al., "Retinal pigment epithelial lipofuscin and melanin and choroidal melanin in human eyes", Invest. Ophthalmol. Vis. Sci., vol. 27, No. 2, Oct. 1986, pp. 145-152.

Gabel et al., "Visible and near infrared light absorption in pigment epithelium and choroid", Proceedings of the 23rd International Congress of Ophthalmology, 1979, pp. 658-662.

Jang et al., "Characterization of peroxy-A2E and furan-A2E photooxidation products and detection in human and mouse retinal pigment epithelial cell lipofuscin", J. Biol. Chem., vol. 280, No. 48, Dec. 2005, pp. 39732-39739.

Pengo et al., "Efficient blind spectral unmixing of fluorescently labeled samples using multi-layer non-negative matrix factorization", PLoS One, vol. 8, No. 11, Nov. 2013, 11 sheets.

\* cited by examiner

METHOD AND SYSTEM FOR SIMULTANEOUS DECOMPOSITION OF MULTIPLE HYPERSPECTRAL DATASETS AND SIGNAL RECOVERY OF UNKNOWN FLUOROPHORES IN A BIOCHEMICAL SYSTEM

PRIORITY CLAIM

This application claims priority to U.S. Provisional Application Ser. No. 62/064,851 filed Oct. 16, 2014, the entire contends of which is hereby incorporated by reference herein.

GOVERNMENT FUNDING

This invention was made with government support under Grant Nos. NIH/NEI Grant RO1 EY015520, NIH/NEI R01 EY021470 and NIH/NEI R01 EY06109. The U.S. government has certain rights in the invention.

FIELD OF INVENTION

The present invention relates generally to fluorescent imaging of a mixture of fluorophores in a biochemical system, for example, fluorescent imaging of fluorophors in an eye.

BACKGROUND

Age-related macular degeneration (AMD) has been a major cause in untreatable vision loss and blindness. AMD is a disease of the photoreceptor system in the eye, including undesirable changes to the retinal pigment epithelium (RPE). The RPE is a monolayer of pigmented epithelial cells directly beneath the photoreceptors of the neural retina. It rests on Bruch's membrane (BrM), a 5-layered extracellular matrix, which functions as both the substrate for RPE attachment and as a vessel wall at the inner aspect of the choroidal vasculature that nourishes RPE and photoreceptors. Changes in the RPE are considered to be central to the initiation and progression of age-related macular degeneration, a major cause of vision loss in the elderly in the industrialized countries today. The RPE has an innate autofluorosecence; the normal pattern of this fluorescence is altered in AMD in characteristic ways. Therefore, there is a need for a device that provides for imaging, quantifying and analyzing the autofluorescence of the eye, particularly in the RPE and/or BrM, to further study and identify the biologic and/or molecular basis for AMD.

SUMMARY OF THE INVENTION

In accordance with the foregoing objectives and others, one embodiment of the present invention provides systems and methods for analyzing fluorescence of fluorophors in an eye. The fluorophors may include lipofuscins, for example, lipofuscins endogenously generated in a retinal pigment epithelium (RPE). In some embodiments, the lipofuscins may include A2E (n-retinylidene-n-retinyl ethanolamine).

In one aspect, a method for analyzing fluorescence of fluorophors in an eye is provided. The method includes the step of obtaining, from a plurality of hyperspectral sensors, a first data matrix representative of a first electromagnetic emission spectrum from the fluorophors in response to an excitation signal. The method also includes the step of isolating a second data matrix from the first data matrix, the second data matrix being representative of a second electromagnetic emission spectrum from a RPE of the eye in response to the excitation signal. The method further includes the step of identifying one or more Gaussian functions, wherein each Gaussian function is an initial approximation representative of a spectral component of the second electromagnetic emission spectrum. The method further includes the step of analyzing the second data matrix using non-negative matrix factorization initialized with the one or more Gaussian functions to generate one or more component matrices, wherein each component matrix is a second approximation representative of the corresponding spectral component of the second electromagnetic emission spectrum. In some embodiments, the method may further includes the step of generating a two-dimensional image from one of the component matrices, wherein the two-dimensional image approximately corresponds, in part, to a histological image of the eye. In one embodiment a composite of the one or more Gaussian functions approximates the second data matrix. In another embodiment, the number of Gaussian functions corresponds to the number of peaks within the second electromagnetic emission spectrum. In a further embodiment, the method may also include the step of quantifying the amount of lipofuscin present in the RPE based on an intensity of one of the spectral components represented by the corresponding component matrix.

In another aspect, a method for analyzing fluorescence of fluorophors in an eye is provided. The method includes the step for obtaining, from a plurality of hyperspectral sensors, a first data cube representative of first electromagnetic emission spectra from the fluorophors in response to excitation signals having two or more different wavelengths. The method also includes the step for isolating a second data cube from the first data cube, the second data cube comprising a plurality of data matrices, each data matrix being representative of an individual emission spectrum from a RPE of the eye in response to the excitation signal at each of the different wavelengths. The method further includes the step for identifying one or more Gaussian functions for each data matrix, wherein each Gaussian function is an initial approximation representative of a spectral component of the corresponding individual emission spectrum. The method further includes the step for analyzing the second data cube using non-negative tensor factorization initialized with the one or more Gaussian functions for each data matrix to generate one or more component matrix functions, wherein the component matrix functions are concatenated across the plurality of data matrices such that each component matrix function is a common approximation representative of each corresponding spectral component shared across each individual emission spectrum. In some embodiments the method may further comprise the step of generating a two-dimensional image from one of the component matrix functions, wherein the two-dimensional image approximately corresponds, in part, to a histological image of the eye. In other embodiments, the excitation signals may have three or more different wavelengths. In a different embodiment, a composite of the one or more Gaussian functions for each data matrix approximates the corresponding data matrix. In a further embodiment, the number of Gaussian functions for each data matrix corresponds to the number of peaks within each individual emission spectrum. In another embodiment, the method may further include the step of quantifying the amount of lipofuscin present in the RPE based on an intensity of one of the spectral components represented by the corresponding component matrix.

In a further aspect, a hyperspectral imaging device for detecting fluorophors in an eye is provided. The device includes a light source configured to deliver an excitation signal to the eye. The device also includes a hyperspectral sensor configured to collect hyperspectral data in a first data matrix representative of a first electromagnetic emission spectrum from the fluorophors in response to the excitation signal. In some embodiments, the hyperspectral sensor may be a hyperspectral camera, such as a scanning laser ophthalmoscope or a fundus camera. The device further includes a processing arrangement configured to isolate a second data matrix from the first data matrix, the second data matrix being representative of a second electromagnetic emission spectrum from a retinal pigment epithelium (RPE) of the eye in response to the excitation signal. The device also includes an analyzing arrangement configured to identify one or more Gaussian functions, wherein each Gaussian function is an initial approximation representative of a spectral component of the second electromagnetic emission spectrum, and analyze the second data matrix using non-negative matrix factorization initialized with the one or more Gaussian functions to generate one or more component matrices, wherein each component matrix is a second approximation representative of the corresponding spectral component of the second electromagnetic emission spectrum. In some embodiments, the device further comprises an imaging arrangement configured to generate a two-dimensional image from one of the component matrices, wherein the two-dimensional image approximately corresponds, in part, to a histological image of the eye.

These and other aspects of the invention will become apparent to those skilled in the art after a reading of the following detailed description of the invention, including the figures and appended claims.

DETAILED DESCRIPTION

Figure 1A:
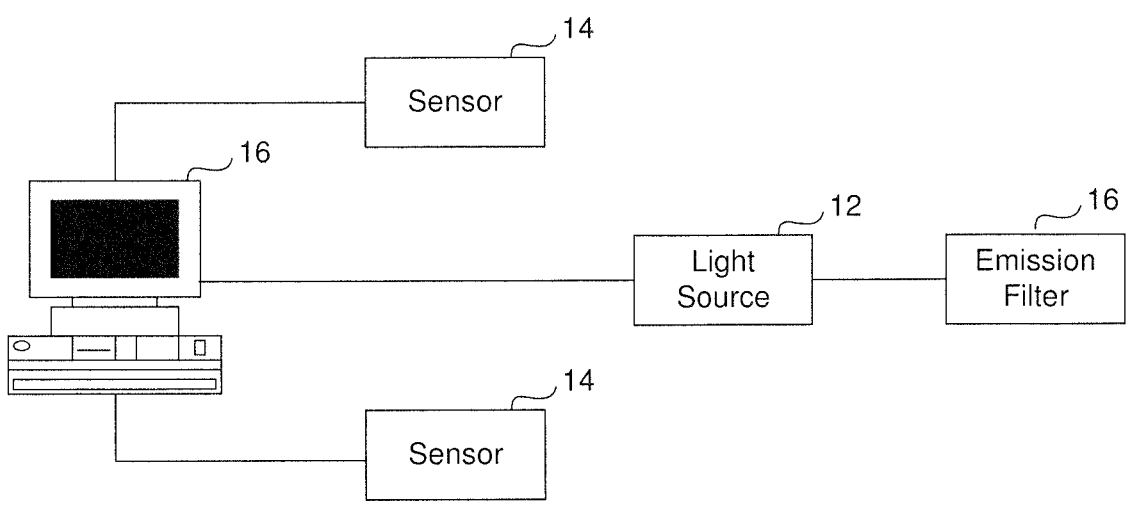
FIG. 1A shows an exemplary hyperspectral imaging device 10 for analyzing fluorescence of fluorophors in an eye.

The RPE is responsible for generating vitamin A derivatives required for phototransduction, the initials steps of vision, through a series of biochemical steps called the visual cycle. Byproducts of the visual cycle are thought to aggregate in the lysosomal compartment of the RPE, as lipofuscin, which has an intense fluorescent signal. Because this signal comes from endogenous substances, rather than, for example, exogenously introduced fluorescent markers, it may be referred to as lipofuscin autofluorescence (AF). It is believed that, first, lipofuscin AF presents a single broad emission spectrum, which is believed to be a sum total of multiple constituents; second, knowing the true molecular constituents of this peak is considered vital to understanding the role of the RPE in health and disease. The fluorophore known as A2E (n-retinylidene-n-retinyl ethanolamine) was previously reported as being dominant in the RPE. However, imaging mass spectroscopy shows that A2E has strong regional variations in its tissue distribution and suggesting that multiple additional essential compounds may contribute to disease of the eye. It is therefore, an objective of the present invention to provide methods capable of identifying and extracting plausible, abundant fluorophore signals.

In one embodiment, a hyperspectral imaging device 10 for detecting fluorophors in an eye may be provided. The device 10 may include a light source 12 for delivering an excitation signal to the eye. The light source 12 may be connected to a processing arrangement 16 configured to receive signals instructing the light source 12 for providing an excitation signal (e.g., deliver an excitation light) to the eye. The excitation signal may be a light at any suitable wavelength. It may be coupled to a suitable long pass emission filter 16 that blocks reflected light from the eye, and allows only the fluorescent signal from the eye to return. This fluorescent signal is then captured by one or more hyperspectral sensors 14, for example, in 10 nm intervals between 420 nm and 720 nm, or between 510 and 720 nm. In other exemplary embodiments, the light source 12 may provide an excitation signal having a wavelength of 320 nm, 436 nm and/or 480 nm. In a further exemplary embodiment, the excitation signals may be provided in two excitation bands, e.g., 436-460 nm and 480-510 nm. In one particular embodiment, the excitation bands may be at two different wavelengths, e.g., 436 nm and 480 nm, and the emissions spectra may be captured between 420-720 nm and between 510-720 nm, respectively at 10 nm intervals.

Fluorophore Signal Recovery in the Human Retinal Pigment Epithelium (RPE)

The RPE is a single layer of cells in the eye. The RPE emits a strong fluorescent signal used in diagnostics and clinical management of retinal disease. Upon excitation with different wavelengths of light, biological tissues emit distinct but related autofluorescence signals. FIG. 1A shows an exemplary hyperspectral imaging device 10 for analyzing fluorescence of fluorophors in an eye. The hyperspectral imaging device 10 may include one or more hyperspectral sensors 14 for collecting hyperspectral data from the fluorophors in the eye. The sensors 14 may be connected to the processing arrangement 16. The sensors 14 may be configured to transmit to the processing arrangement 16 hyperspectral emissions data measured from the eye.

In one embodiment of the hyperspectral imaging device 10, the hyperspectral sensors 14 may be included in a hyperspectral camera, such as a hyperspectral fundus camera, used to capture emission from the fluorophors. The emissions from the fluorophors may correspond to data in any suitable form, including for example, in the form of a data matrix or a data cube. For patients, a snapshot system is preferable to sequential filter sets, both for patient tolerability and for image registration, which is used to correct misalignment in sequential images caused by patient eye movement. In some embodiments, the hyperspectral sensors 14 may be included in a scanning laser opthalmoscope (SLO), more particularly a confocal scanning laser ophthalmoscope (cSLO), such as the Heidelberg Engineering Spectralis SLO. The SLO or cSLO may also include a snapshot acquisition "per frame" for all wavelengths, and then the average of the snapshots. This average is particularly useful for systems with a low signal to noise ratio where multiple images may be acquired and an average of the images are obtained to identify and eliminate noise from the images. The hyperspectral sensors may also be included in a fundus camera, such as the standard fundus camera adapted for detecting AF from Topcon (e.g., Topcon TRC-501X) or from Zeiss (e.g., Zeiss FF 450 Plus IR). In one particular embodiment, the hyperspectral sensors may be included in a fluorescence microscope, such as a Zeiss Axio Imager A2 microscope. With a single flash, a non-confocal image may be captured as a snapshot hyperspectral image. With non-confocal imaging, an image of the fluorescence may be captured for everything, including the lens, and thus, corrections would need to be made. With confocal imaging, only RPE fluorescence is captured and other sources such as the lens are rejected. The lens AF spectrum may be separated from the RPE signal. Other spectral data, e.g., fundus reflectance, may be used to correct for lens absorbance.

Since both RPE and BrM have intrinsic autofluorescence properties, and RPE anatomically overlies BrM, the hyperspectral data cubes may capture the sum of both signals. Hence, to assist in identifying the pure RPE spectrum at each location, a pure BrM signal without overlying RPE cells may also be recorded separately. The pure BrM signal may be obtained in ex vivo samples from areas where a few RPE cells were dislodged during preparation. For locations at which the RPE monolayer is completely intact, a pure BrM signal may be separately imaged at an adjacent area.

The hyperspectral imaging device 10 may further include any suitable processing arrangement 16 for controlling the light source and/or one or more sensors 14, and may further analyzing these autofluorescence signals. Those skilled in the art will understand that the exemplary embodiments described herein may be implemented in any number of manners, including as a separate software module, as a combination of hardware and software, etc. For example, the exemplary analysis methods may be embodiment in one or more programs stored in a non-transitory storage medium and containing lines of code that, when compiled, may be executed by at least one of the plurality of processor cores or a separate processor. In some embodiments, a system comprising a plurality of processor cores and a set of instructions executing on the plurality of processor cores may be provided. The set of instructions may be operable to perform the exemplary methods discussed below.

Figure 8:
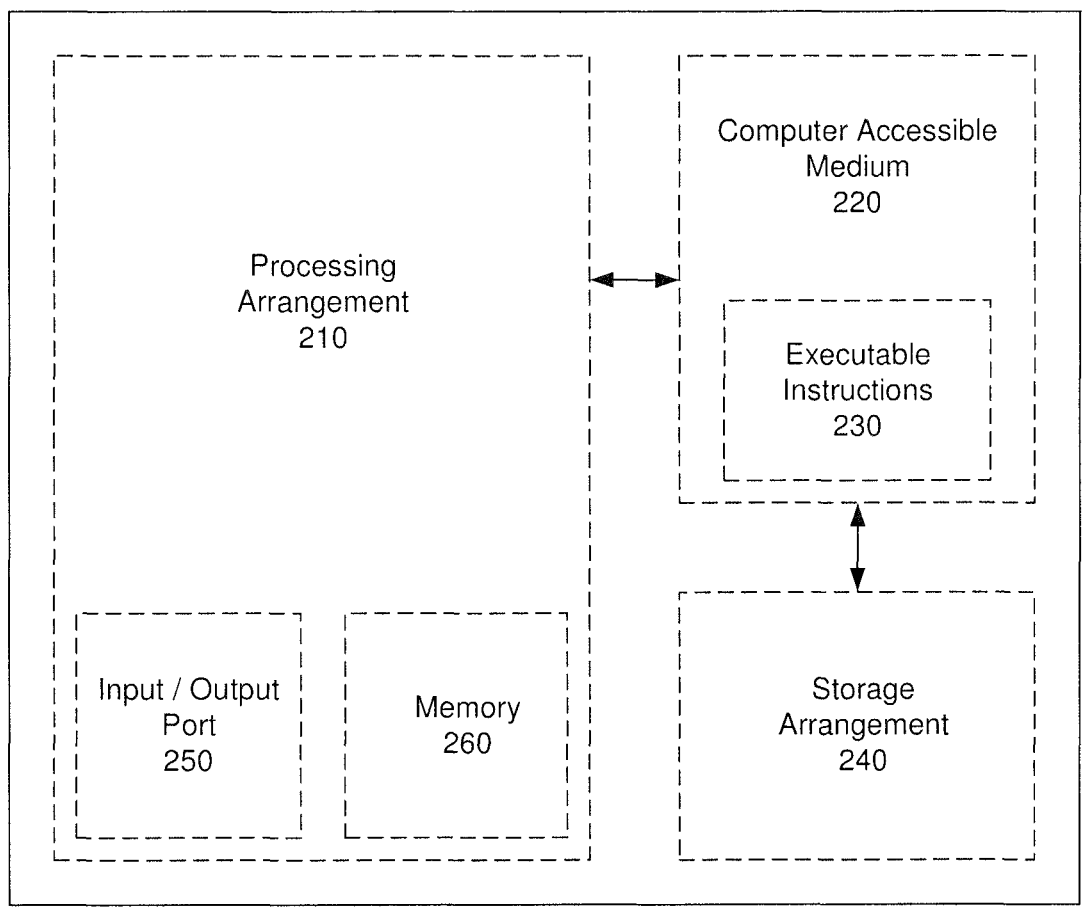
FIG. 8 illustrates an exemplary computer system for performing method for analyzing fluorescence of fluorophors in an eye.

For example, the exemplary analysis methods may be embodied in an exemplary system 200 as shown in FIG. 8. For example, an exemplary method described herein may be performed entirely or in part by a processing arrangement 210. Such processing/computing arrangement 210 may be, e.g., entirely or a part of, or include, but not limited to, a computer/processor that can include, e.g., one or more microprocessors, and use instructions stored on a computer-accessible medium (e.g., RAM, ROM, hard drive, or other storage device). As shown in FIG. 8, e.g., a computer-accessible medium 220 (e.g., as described herein, a storage device such as a hard disk, floppy disk, memory stick, CD-ROM, RAM, ROM, etc., or a collection thereof) can be provided (e.g., in communication with the processing arrangement 210). The computer-accessible medium 220 may be a non-transitory computer-accessible medium. The computer-accessible medium 220 can contain executable instructions 230 thereon. In addition or alternatively, a storage arrangement 240 can be provided separately from the computer-accessible medium 220, which can provide the instructions to the processing arrangement 210 so as to configure the processing arrangement to execute certain exemplary procedures, processes and methods, as described herein, for example.

System 200 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

The excitation of RPE autofluorescence with multiple wavelengths gives rise to different but closely related spectral data emitted from the same cellular structures. To study these relationships, two hyperspectral datasets may be simultaneously decomposed into major spectral signatures with identical spatial distributions and the results may be compared to those of factoring any single hypercube. In an exemplary embodiment, non-negative matrix factorization (NMF) may be used to simultaneously decompose co-registered hyperspectral emission data from an eye, for example, human retinal pigment epithelium/Bruch's membrane specimens, that is illuminated at different wavelengths of light. NMF is an unsupervised machine learning method that may be applied to hyperspectral data for recovering constituent source spectra and the spatial distributions of these components. Traditionally, the NMF method initialized with random spectra converges to a solution by minimizing an error criterion under either a constraint or update rule that enforces only non-negativity. Thus, no information about the structure of the spectral shape of the components is typically employed in the basic NMF algorithm. However, it is believed that biological fluorophores that are histologically and clinically meaningful have emission spectra that have relatively smooth single peaks. Therefore, in some embodiments, the NMF method may be initialized with an estimated Gaussian mixture of components before letting it minimize the error on its own.

Spatially Constrained Simultaneous NMF of Multiple Related Hyperspectral Datasets When tissue is excited at a given wavelength lambda ($\lambda$), hyperspectral emission data may be acquired as an M×N hypercube $X_\lambda$, where M is the number of pixels per image (dimension of spatial information) and emission data are captured from each pixel at N wavelengths (dimension of spectral information). Standard NMF then factors $X_\lambda$ into the product of matrices $A_\lambda$ and $S_\lambda$:

$$X_\lambda = A_\lambda S_\lambda$$

where $S_\lambda$ is a K×N matrix that carries K spectra (the recovered sources), each of which is a feature vector of emissions at N wavelengths, and $A_\lambda$ is an M×K matrix that carries their spatial localizations (abundance images). In one embodiment, an adaptation of non-negative tensor factorization (NTF) considers n such datasets acquired from the same tissue at excitation wavelengths $\lambda_i \ldots \lambda_n$ and assume that based on evidence from pre-existing models or other conditions seeks a fixed number k=K of emission spectra $S_\lambda = [s^\lambda_1, s^\lambda_2, \ldots s^\lambda_k]^T$ for each $\lambda$. Each $s^\lambda_i$ is thus a column vector representing the $i^{th}$ spectral source from excitation wavelength $\lambda$, and the elements $s^\lambda_i$ are naturally and physiologically ordered by increasing peak wavelength.

In one particular embodiment, these spectra may be related by having the same sources for each j, where $1 \le j \le k$. More particularly, for each j, where $1 \le j \le k$, the spectral emissions $s^\lambda_j$ for all excitations $\lambda$ may derive from the same molecular source. In the language of the NMF decomposition, the spatial source distributions $A_\lambda$ of these signals must then be constrained to be exactly the same, because they come from the same compound. Therefore, the factorization may be written as:

$$A \text{ and } [S_{\lambda_1} S_{\lambda_2} \ldots S_{\lambda_n}][X_{\lambda_1} X_{\lambda_2} \ldots X_{\lambda_n}] = A [S_{\lambda_1} S_{\lambda_2} \ldots S_{\lambda_n}]$$

where all excitation datasets are concatenated into a single M×N×n dimensional hypercube on the left. On the right, the solution A is an M×K matrix that is the same for all $\lambda$, and the recovered sources for each excitation are also concatenated as a single K×M×n matrix. Subsequently, A and $[S_{\lambda_1} S_{\lambda_2} \ldots S_{\lambda_n}]$ may be solved or approximated with any suitable NMF method, such as alternating least square, amongst other methods for solving NMF matrices. This method is also referred herein as the concatenated NMF or the non-negative tensor factorization (NTF) solution.

Figure 1B:
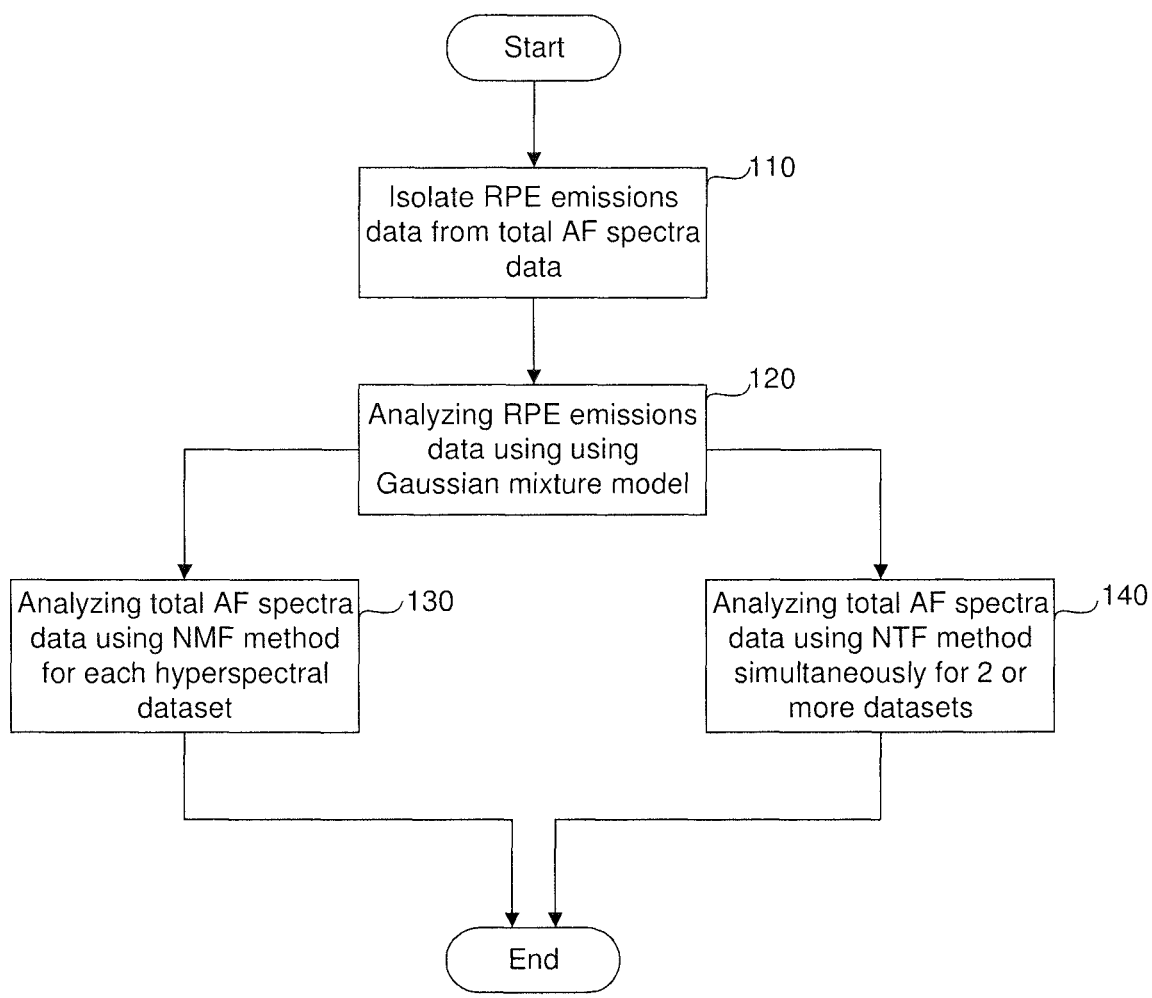
FIG. 1B shows an exemplary method for analyzing fluorescence of fluorophors in an eye.

FIG. 1B illustrates an exemplary method 100 for analyzing fluorescence of fluorophors in an eye, for example a specimen of the RPE or a specimen having combination of the RPE with the BrM. In step 110, data representing a spectrum or a plurality of spectra that are only attributable to the RPE may be isolated. The data may be in the form of a data matrix or a data cube comprised of two or more data matrices. In an exemplary embodiment, the data cube may comprise of a plurality of data matrices, each data matrix representing a spectrum generated at a specific excitation wavelength. In an exemplary embodiment, electromagnetic emissions for a flatmount of RPE attached to Bruch's membrane may be obtained. To obtain a spectrum that is only attributable to the RPE, an emission signal for the BrM may be obtained. In some embodiments, the emission signal from the BrM may be read in tandem with that from RPE. The emission signal from the BrM may be subtracted from the emission signal of the flatmount to arrive at a net signal from the RPE itself.

In step 120, each of the pure RPE spectrum (i.e., a spectrum that is only attributable to the RPE) may be analyzed using a Gaussian mixture model. For example, one or more Gaussian functions may be fitted to each of the pure RPE spectrum. More particularly, the number of Gaussian functions may correspond to the number of peaks within each of the pure RPE spectrum. For example, a pure RPE spectrum with 4 peaks may be fitted with 4 different Gaussian functions. It is noted that there may be no prior knowledge of the number of peaks present in the RPE spectrum. The number of Gaussian functions may be determined empirically based on the experimental data.

In step 130, the data obtained by the hyperspectral sensors from the eye may be analyzed using an NMF method to decompose the emission data from each excitation wavelength. The NMF method may be randomly initialized. Alternatively, the NMF method may include a supervision step or steps. In one step, the NMF may be initialized with the individual Gaussian curves obtained from step 120. Additionally, the NMF method may be initialized with the emission signal from a region in which BrM had been completely exposed. Because the BrM underlies the RPE, the total emission spectrum includes this BrM signal as a component. Typically, NMF initialized with random spectra recovers spectral components that are sometimes jagged, may contain numerous peaks, and may not be readily interpretable given the known histology of these samples. However, decomposed spectra derived from NMF when initialized with the Gaussian spectra estimated from the mixture model fit have been observed to be generally smoother and contained fewer peaks, thus producing a more physiologic solution.

For each emissions spectrum obtained at a select wavelength, the method may analyze data representing each emissions spectrum to solve for one or more matrices representing each spectral component of the spectrum. The combination of these spectral components closely resembles the measured data, for example, within 95% confidence. A two-dimensional abundance image of the emissions spectrum obtained at the select wavelength may be generated from each of the matrices representing spectral component of the spectrum. The image may approximately correspond to, in part, to a histological image of the eye. In some embodiments, a composite of all of these two-dimensional abundance images of the emissions spectrum will closely resemble the histological image of the eye.

In an alternative embodiment, at least two different sets of data may be obtained by the hyperspectral sensors from the eye, each of the data sets generated in response to an excitation signal, e.g., light, having a different and distinct wavelength. For example, hyperspectral data may be obtained from the eye in response to excitation signals having two different wavelengths, for example, 436 nm or 480 nm. In other embodiments, the excitation signals may have three or more different wavelengths. Steps 110 and 120 may be applied to each data set corresponding to emissions obtained in response to an excitation signal at each wavelength In step 140, the at least two sets of data obtained by the hyperspectral sensors may be analyzed using non-negative tensor factorization initialized with the one or more Gaussian functions for each dataset. It is believed that each signal found at one excitation wavelength may be paired to a signal at a different excitation wavelength, and that the spatial source distributions of these signals must be exactly the same, because they come from the same compound, or family of compounds. Therefore, the two or more datasets for NMF may be concatenated together. For example, the datasets may be linked so that the NMF solves for a common set of matrix functions representing the spectral components for each of the datasets. In some embodiments, the NMF analysis is performed simultaneously on the two or more datasets. More particularly, the simultaneous solutions may be constrained to have the same abundances. However, the solutions need not be constrained by any spectral or spatial characteristics, except that the abundance images for the two or more datasets are held to be the same. The combination of these spectral components may closely resemble the measured data obtained from each of the excitation wavelength. In some embodiments, the combination of these spectral components falls within 95% confidence of the measured data. A two-dimensional abundance image of the emissions spectrum obtained at the select wavelength may be generated from each of the matrices. The image may approximately correspond to, in part, to a histological image of the eye. In some embodiments, a composite of all of these two-dimensional abundance images of the emissions spectrum will closely resemble the histological image of the eye.

Each of the different fluorescence components may be further analyzed by comparing the location of their peaks and by their shapes, e.g., single peak vs. multiple peaks. In some embodiments, the spectral shapes may be further compared by a spectral angle distance (SAD) factor, which is a geometric interpretation for such a correlation. For example, for two different spectra S and $\hat{S}$, the SAD may be as follows:

$$SAD(\hat{S}, S) = \cos^{-1}\left(\frac{S^T \hat{S}}{\sqrt{S^T S}\sqrt{\hat{S}^T \hat{S}}}\right),$$

where $S^T$ is the transpose of S. This angle may take the value 0 if the spectra are perfectly correlated and may take a maximum value of $\pi/2$ (or 90 degrees) if the spectra are completely uncorrelated.

Moreover, the abundance images may be overlayed with a suitable image manipulation program, such as, for example, Photoshop CS4 Extended by Adobe Systems, San Jose, Calif. For example, standard colors (not the wavelengths of the emissions) may be assigned to each of the overlaid signal abundances, to provide a visually intuitive interpretation of co-localizations and relative intensities. More particularly, if one signal abundance is assigned the color green, and another red, then areas where they co-localize will appear yellow, or perhaps orange if the red signal is more abundant. Tissue co-localizations of the abundances (spectral sources) may also be calculated quantitatively using the Pearson correlation coefficient. For tissues in which patches of bare BrM were present, a mask may be first applied to eliminate BrM from the calculation of correlations.

It is believed that identification of the different fluorescence components, such as lipofuscin and melanolipofuscin, in eye tissue may improve diagnosis and further identify the mechanisms for vision loss and other eye diseases, such as AMD, diabetic retinopathy, retinal degenerations such as Stargardt disease and retinitis pigmentosa amongst others. For example, the spectral intensity of the signals may be measured by the sensor in the device in units of photons per sec. The same acquisition system may also measure the signal from a fixed fluorescent reference material, so that the tissue signal can be compared to or calibrated to this fixed signal for quantification of an amount, concentration and/or distribution of fluorophors present in the tissue. The amount of lipofuscin and/or melanolipofuscin, or the individual components thereof, may then be directly proportional to the intensity of the signal of each component. It is believed that the amount of lipofuscin and/or melanolipofuscin detected may reflect the state of AMD disease progression in the eye. In a healthy eye, lipofuscin accumulates uniformly throughout life. In an AMD eye, there are areas of increased and decreased lipofuscin, and measuring these amounts provides metrics for disease progression. When the individual component fluorophores of lipofuscin are measured, it provides a quantifiable metric for assessing how much of the eye is healthy/harmless and which part is predictive of disease progression.

The present invention may also be useful in monitoring the response to treatment of these disorders in clinical trials, providing more precise and quicker outcome metrics. The present invention may also assist in providing a complete histological mapping of the eye, including but not limited to circulation in eye tissue. In particular, oxygenation and deoxygenation of eye tissue may be visualized by sensing and analyzing emissions of oxyhemoglobin and deoxyhemoglobin, by using the device in hyperspectral reflectance mode. In this mode, the characteristic absorption spectra of these molecules can be identified and quantified by NMF. Once the relative quantities of each are determined, the $O_2$ saturation of the tissue can be calculated by using any suitable method.

EXAMPLES

Figure 7A:
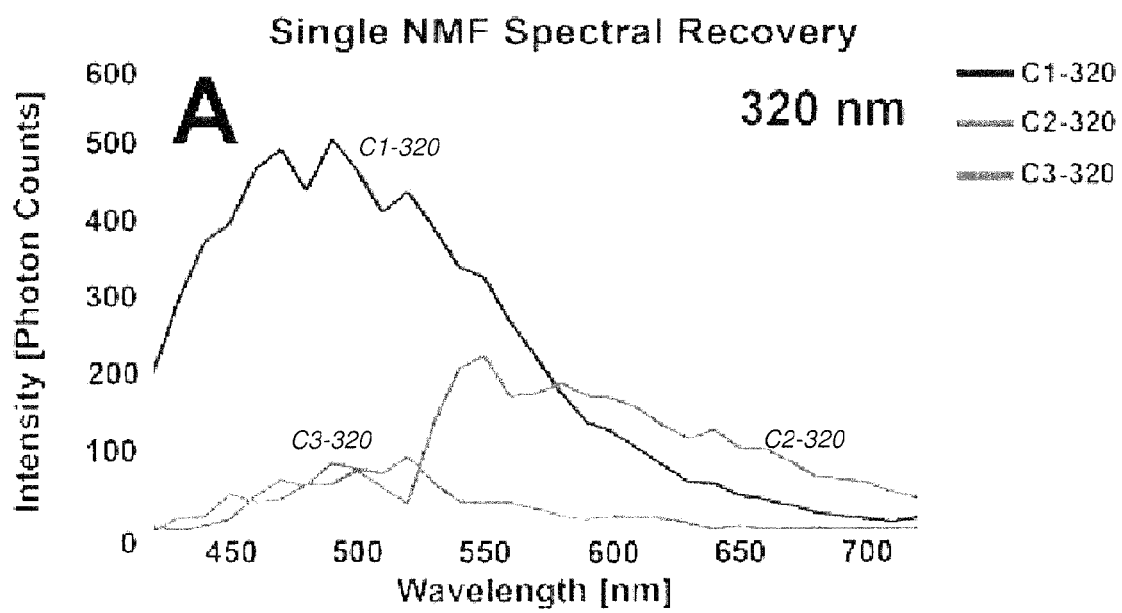
FIG. 7A illustrates an exemplary embodiment of spectral components generated using a single NMF spectral recovery method (e.g., decomposed from exemplary individual excitation datasets) obtained from an exemplary BrM spectrum received from 320 nm excitation.
Figure 7B:
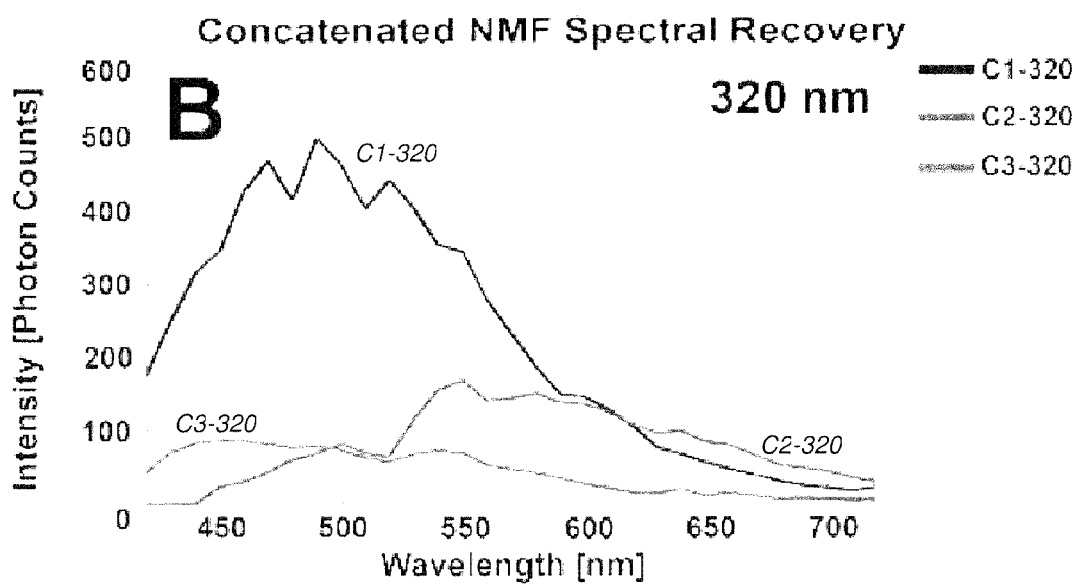
FIG. 7B illustrates an exemplary embodiment of spectral components generated using a concatenated NTF spectral recovery method (e.g., decomposed from simultaneous solution of three exemplary datasets) obtained from an exemplary RPE spectrum received from 320 nm excitation.

As shown below in Example I, simultaneous decomposition of multiple hyperspectral datasets constrained by common abundant sources may offer in some cases a superior method than standard NMF at breaking down a complex spectrum into its individual spectral signals. The greater information content as well as strong spatial constraint can assist in finding an improved physical solution to what is notoriously a massively underdetermined problem. A clearer outcome may also be aided with improved signal to noise ratio (SNR), for example in the Example II, where the abundances of the weaker UV excited signals were significantly improved by tying them to those of two stronger signals (FIGS. 7A and 7B).

This approach has not been previously applied to search for multiple spectra that are initially completely unknown. Furthermore, the fluorescent label problem by its nature seeks abundances that are largely distinct, because the individual labels are believed to bind to distinct cellular structures. In the RPE samples of Example I, the individual fluorophores all localize to lipofuscin and melanolipofuscin granules. This is demonstrated in the histological images or abundance images that show where the sources of fluorescence are localized. The NMF method separates the totality of emission data into two blocks of data, spectral and spatial. These blocks provide answers to the two questions of interest—i.e., what are the strongest spectra in the total emission, and where are they coming from spatially—and are visualized as a set of spectra and another set of corresponding abundance images. Therefore, there is a need to separate the separate the sources, constrain the NMF solution, and assist in correct spectral resolution.

Indeed, the non-negativity constraint may provide a unique decomposition if 1: there is spectral separation of a precise nature, i.e., although spectra can overlap to an extent, when a given individual spectrum is compared to the group of other spectra, there must be at least one channel outside the given spectrum that is in common with the overlap of all the other spectra, and 2: there is spatial separation, i.e., the image has to contain pixels in which one source is absent and others are present in various concentration ratios. Conversely, to the extent these conditions are not obtained, i.e., where label distributions are similar and spectra overlap strongly, uniqueness fails. In the case of RPE or BrM spectra shown below in Examples I and II, neither of these conditions is met: all Gaussian candidate spectra overlap already at initialization, as do the recovered spectra in almost every case, and, as just mentioned, the abundances of the respective RPE signals are virtually identical except for magnitude. Nonetheless, in the following examples of two tissue types (RPE and BrM), the recovered signals from simultaneous decomposition of multiple hyperspectral AF datasets appeared to provide consistent and better candidates for biochemical identification, further attesting to the strength of the method when applied to a historically difficult problem. In conclusion, it is believed that NTF with concatenated excitation data sets offers improved spectral recovery, even in challenging domains with unknown and overlapping spectra that are also poorly separated spatially.

Example I

RPE Spectra from 2 Excitation Datasets

Sample Preparation and Microscopy

The autofluorescence spectrum of twenty flatmounts of human RPE attached to Bruch's membrane (RPE/BrM) without any retinal pathology was acquired and measured. The flatmounts were prepared as previously described. From chorioretinal tissue, retina and choroid were gently removed to prepare 20 μm thin RPE/BrM flatmounts. During tissue preparation, images were taken from every preparation step to maintain the position of the fovea of the retina, the site of high acuity central vision.

Three different locations on the tissue were chosen for our measurements (distances relative to the fovea): fovea (cone photoreceptors only), 2 mm superior (perifovea; highest rod photoreceptor density), and 10 to 12 mm superior (periphery; highest rod/cone photoreceptor ratio).

Microscopy was performed using Zeiss Axio Imager A2 microscope, equipped with a 40× oil lens (NA=0.75) (both: Carl Zeiss, Jena, Germany), two filter cubes (filter 1: 436/460 nm excitation/long pass emission; filter 2: 480/510 nm excitation/long pass emission; Chroma Technology Corp, Bellows Falls, Vt., US) and connected to an external mercury arc light source (Xcite 120Q, Lumen Dynamics Group Inc., Mississauga, Canada).

At each location, two hyperspectral data cubes of RPE and BrM were acquired using the two different microscope filters and a hyperspectral camera (Nuance FX, Caliper Life Sciences, Waltham, Mass., US), with measurements made at 10 nm intervals between 420 nm and 720 nm, and 510 and 720 nm, respectively. The data in the smaller spectral range was padded with zeroes to create hypercubes with the same spatial and spectral dimensions. Each raw data cube was saved using the integrated software (Nuance 3.0.1.2.) and exported for further NMF analysis. For brevity, the two excitations are referred to herein as 436 nm and 480 nm.

Step 1: Pure RPE Spectrum Separated from Underlying BrM Spectrum

Figure 2:
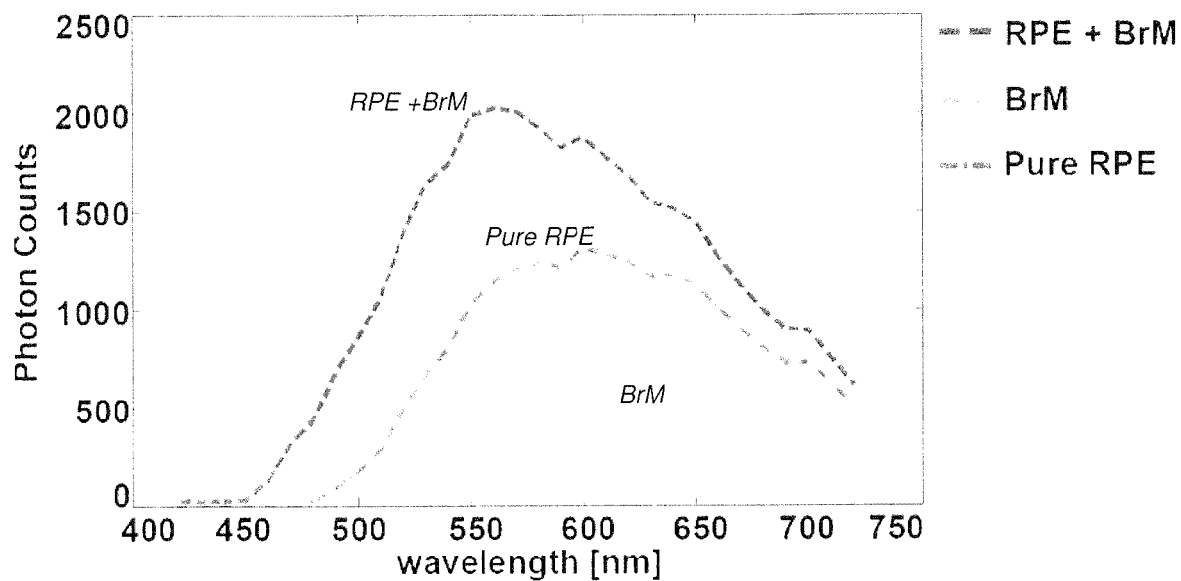
FIG. 2 illustrates an exemplary pure spectrum of the RPE, having separated emissions curves for the exemplary pure RPE from that of BrM.

In accordance with step 110 described above, the emission signal from a patch of pure BrM, read in tandem with that from RPE, was subtracted to give a net signal from the RPE itself. FIG. 2 illustrates an exemplary pure spectrum of the RPE a 49 year-old male donor obtained in response to an excitation at a wavelength of 436 nm. Sample spectral data were acquired from a region with BrM in isolation and a region with RPE cells containing lipofuscin overlying BrM. In particular, FIG. 2 shows the separated emissions curves for the pure RPE. The emissions curve for an isolated BrM is located at the bottom of FIG. 2. The emissions curve for a RPE combined with a BrM is located at the top of FIG. 2. The emissions curve for a pure RPE signal (subtraction of the two) is also shown in FIG. 2.

Step 2: Gaussian Mixture Modeling

Figure 3:
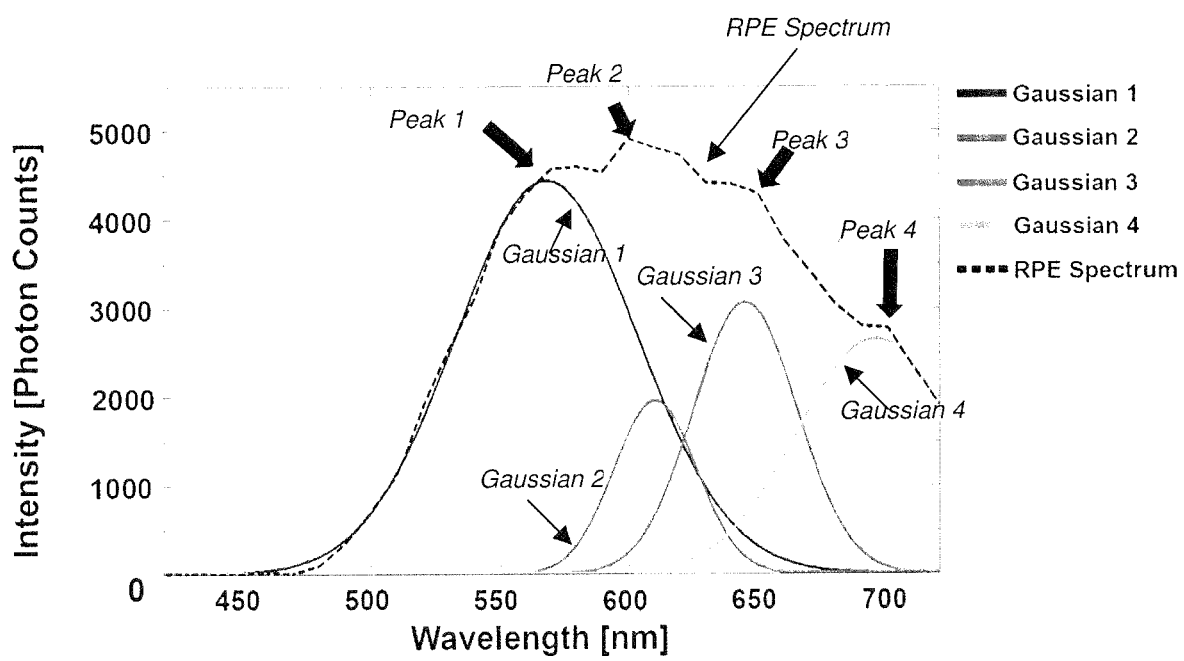
FIG. 3 illustrates exemplary Gaussian model fits to a sample RPE spectrum.

In accordance with step 120 described above, for the pure RPE spectrum at each location for each donor (FIG. 2), Gaussian mixture modeling was applied to extract four candidate spectral components (FIG. 3), which provided single peak, smooth candidates for individual fluorophore components. FIG. 3 illustrates exemplary Gaussian model fits to a sample RPE spectrum. FIG. 3 shows the original RPE hyperspectral data (dotted black line) and the four Gaussian components of the mixture model. The arrows indicate four shoulders or peaks in the original spectrum. The mixture model (sum of 4 Gaussians) largely overlies the original RPE data. The mixture model in this Example I provides 95% confidence prediction bounds of the model under assumption of 5% random error in the original RPE spectrum.

It is important to note that there was no prior knowledge that 4 abundant signals would be present. It was simply observed that recovered spectra contained 4 peaks or shoulders (FIG. 3, arrows) almost universally centered at approximately 575, 600, 640 and 700 nm. Therefore, 4 Gaussian curves were chosen to fit the data throughout. It was also empirically observed that solutions with 3 or 5 Gaussians were unsatisfactory or redundant. All fits were performed by a custom MATLAB program.

Step 3: NMF of Single Excitation Hyperspectral Datasets

In accordance with step 130 described above, NMF was used to decompose the RPE emission hypercubes from each excitation wavelength. In addition to random initialization, this step also included a supervision step, which initialized the spectra as the individual Gaussian curves in the mixture model. In combination with the Gaussian curves, the NMF method was also initialized using the emission signal acquired from a region in which BrM had been completely exposed. Because BrM underlies the RPE, the total RPE emission spectrum includes this BrM signal as a component, as noted above in Step 1. Therefore the NMF method was initialized with 5 spectra in all, the 4 Gaussian curves and the BrM spectrum.

Figure 4A:
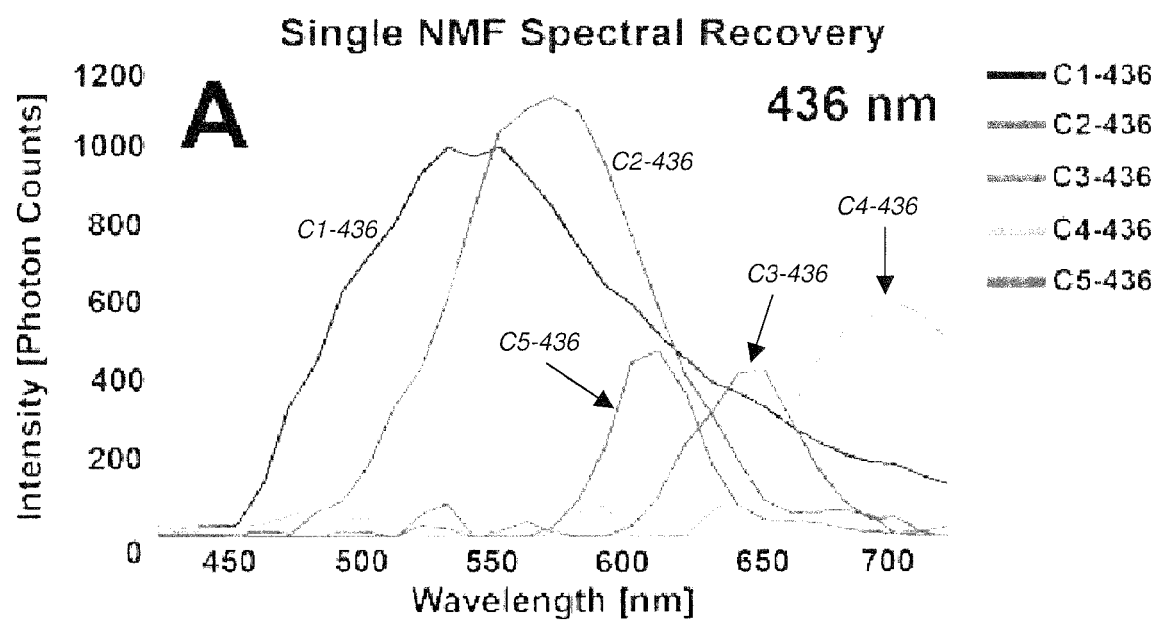
FIG. 4A illustrates an exemplary embodiment of spectral components generated using a single non-negative matrix factorization (NMF) spectral recovery method (e.g., decomposed from exemplary individual excitation datasets) obtained from an exemplary RPE spectrum and BrM spectrum obtained from 436 nm excitation.
Figure 4B:
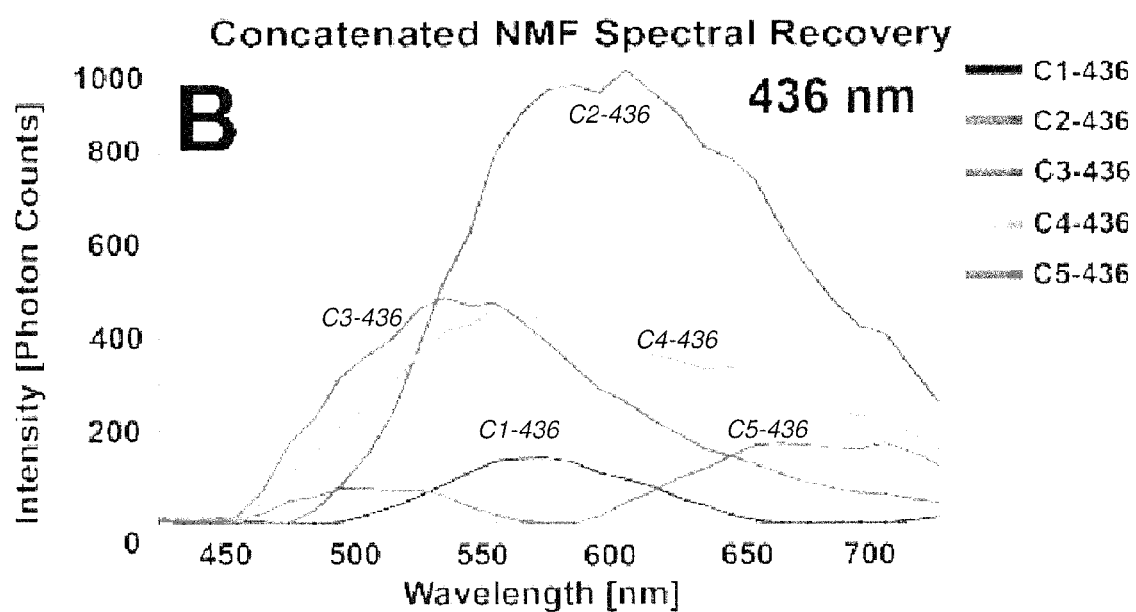
FIG. 4B illustrates an exemplary embodiment of spectral components generated using a concatenated nonnegative tensor factorization (NTF) spectral recovery method (e.g., decomposed from simultaneous solution of two exemplary datasets) obtained from an exemplary RPE spectrum received from 436 nm excitation.
Figure 4C:
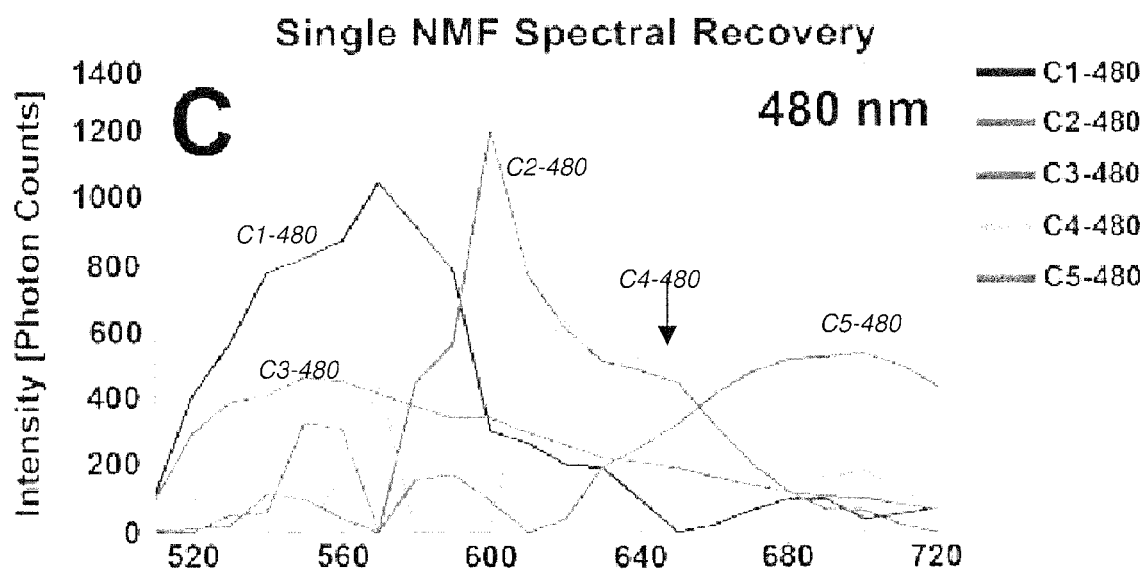
FIG. 4C illustrates an exemplary embodiment of spectral components generated using a single NMF spectral recovery method (e.g., decomposed from exemplary individual excitation datasets) obtained from an exemplary RPE spectrum received from 480 nm excitation.

FIGS. 4A and 4C illustrate each of the components of data generated using a single NMF spectral recovery method. In particular, the spectra in FIGS. 4A and 4C are both decomposed from individual excitation datasets, e.g., data obtained from excitation at a single wavelength. FIG. 4A shows data for a spectrum recovered from 436 nm excitation. FIG. 4C shows data for a spectrum recovered from 480 nm excitation. The tissue image for both FIGS. 4A and 4C is a full 40× field. The 5 individual spectra in each set are labeled C1 to C5. The spectra shown in FIGS. 4A and 4C have multiple subsidiary peaks, suggesting contributions from multiple sources. Those from 480 nm excitation are particularly jagged. The lower right element of each of FIGS. 4A and 4C is the composite RGB image from the total AF signal for that excitation. These images could be directly compared with the original image of the tissue, and these also showed correct histological correspondence (FIGS. 4A and 4C). Thus, the four RPE sources all localized to areas surrounding the nuclei in a manner characteristic of lipofuscin. A fifth spectral component representing the known emission signal for BrM corresponded to abundance images that highlighted regions of exposed BrM (FIGS. 4A and 4C).

Step 4: Spatially Constrained Simultaneous NMF of Multiple Excitation Hyperspectral Datasets: Non-Negative Tensor Factorization (NTF)

In accordance with step 140 described above, RPE/BrM flatmounts were excited at more than one wavelength. As described above, the RPE/BrM flatmounts were excited at both 436 nm and 480 nm, and hyperspectral emission data were captured for both wavelengths. As discussed above in Step 3, 4 spectral signatures for RPE and one for BrM were retrieved for each dataset. It is postulated that each signal found at 436 nm excitation was paired to a signal at 480 nm, and that the spatial source distributions of these signals must be exactly the same, because they come from the same compound. Therefore, the two datasets for NMF are linked with these constraints as described in above with respect to NTF, with n=2 and k=5 in this particular example.

Figure 4D:
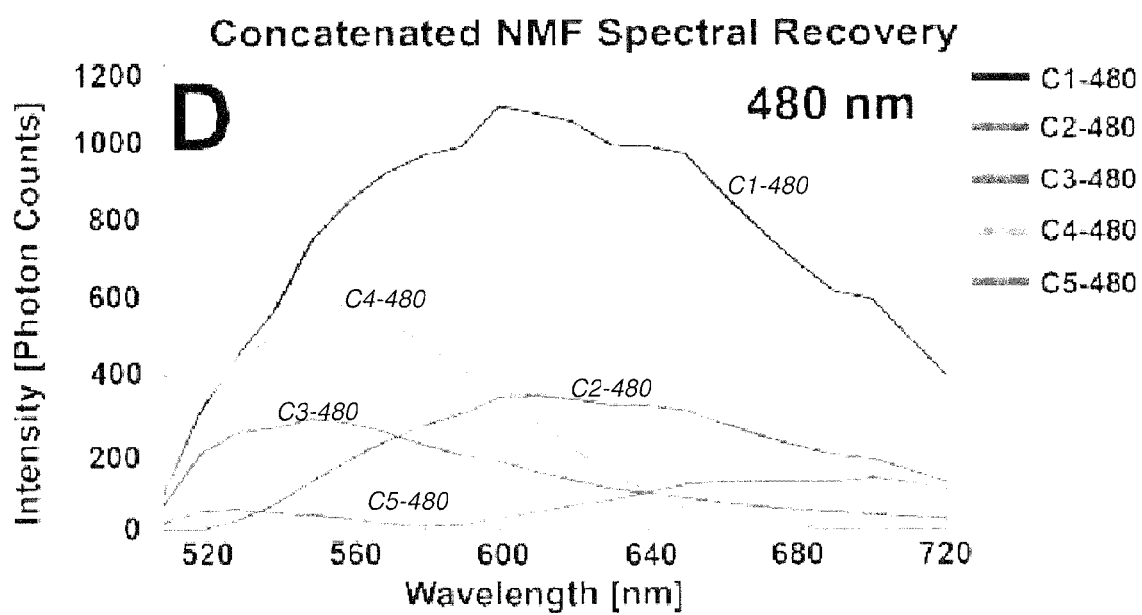
FIG. 4D illustrates an exemplary embodiment of spectral components generated using a concatenated NTF spectral recovery method (e.g., decomposed from simultaneous solution of two exemplary datasets) from an exemplary RPE spectrum received from 480 nm excitation.

FIGS. 4B and 4D shows data for the corresponding spectra found with simultaneous solution of the concatenated datasets. The solutions were initialized with the same Gaussians and BrM spectra used for the individual NMF solutions. In other words, data for the spectra in FIGS. 4B and 4D are both decomposed from simultaneous solution of both excitation datasets, e.g., data obtained from excitation both 436 nm and 480 nm. FIG. 4B shows data for a spectrum recovered from 436 nm excitation. FIG. 4D shows data for a spectrum recovered from 480 nm excitation. The tissue image for both FIGS. 4B and 4D is a full 40× field. The 5 individual spectra in each set are labeled C1 to C5. The corresponding abundance images are also labeled C1 to C5, with false coloring to indicate the relative signal intensities. The spectra shown in FIGS. 4B and 4D are all broad, as expected from known fluorophore data, and can be paired by shape and location. The recovered paired spectra are smoother than either spectrum recovered separately, with more congruent shapes. The lower right element of each of FIGS. 4B and 4D is the composite RGB image from the total AF signal for that excitation. The constrained identical abundance images on the right for each pair of spectra show precise anatomic detail and are more clearly defined than the abundances recovered individually, hence are more consistent with well-defined species of emitter. For example, C3, has an abundance more specific to the area of isolated BrM than its counterparts in the individual cases at both excitation wavelengths. Signals from RPE cells (C1, C2, C4, and C5) can be distinguished from each other by the relative size of the signal-poor region in the center of each hexagonal RPE cell in the concatenated solutions, whereas such distinction between the abundances in the individual solutions. (C2—436 is clearly C1—480; C3 is BrM in each; C4 and C5 correspond in each; C2—480 appears to be the red-shifted version of C1—436).

The improvement of spectral recovery by NTF compared to individual NMF was subjectively defined as significant, moderate, or none by the degree to which: a) the spectra became less jagged (jagged being defined as having sharp peaks and minima); b) the spectra became more single-peaked; c) the total number of spectra that became "better" by the two previous definitions. In FIGS. 4C and 4D, spectra recovered from 480 nm excitation, all signals except C3 are significantly improved; thus, the NTF solution is judged significantly improved.

Figure 5A:
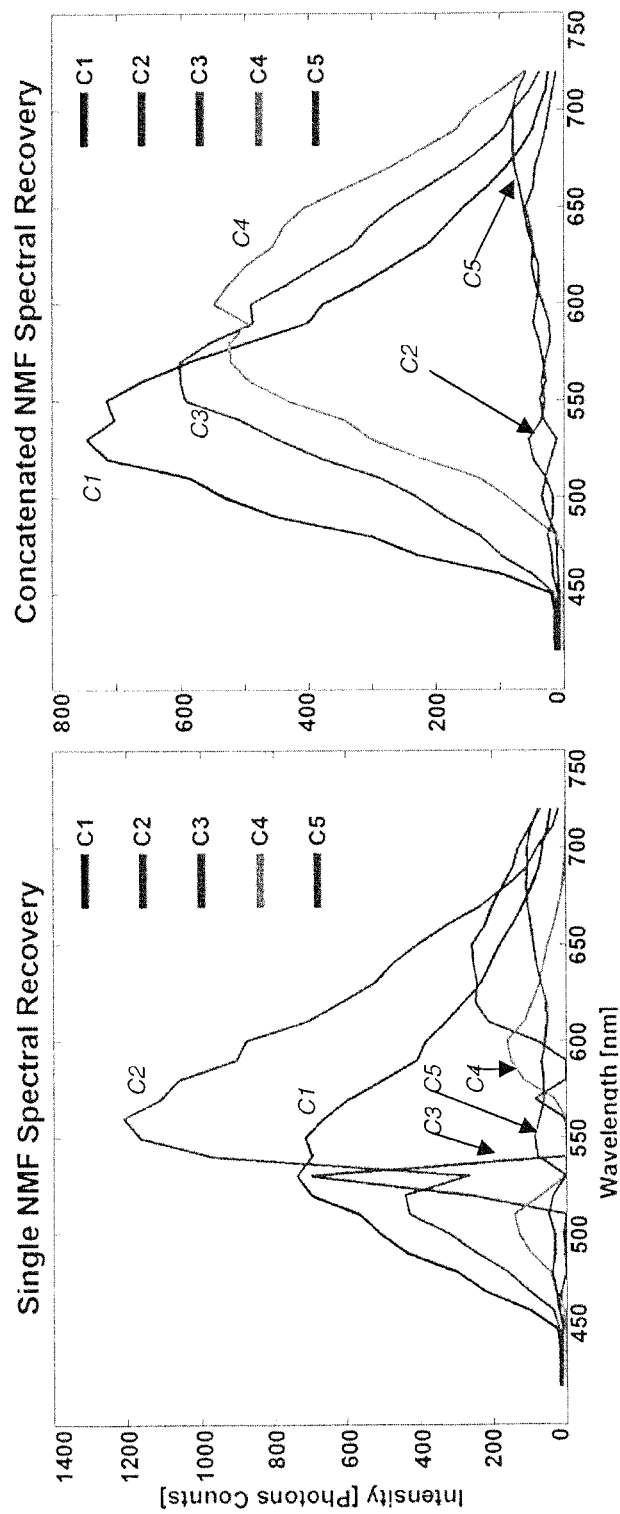
FIG. 5A illustrates examples of moderate improvement in spectral recovery with concatenated NMF.
Figure 5B:
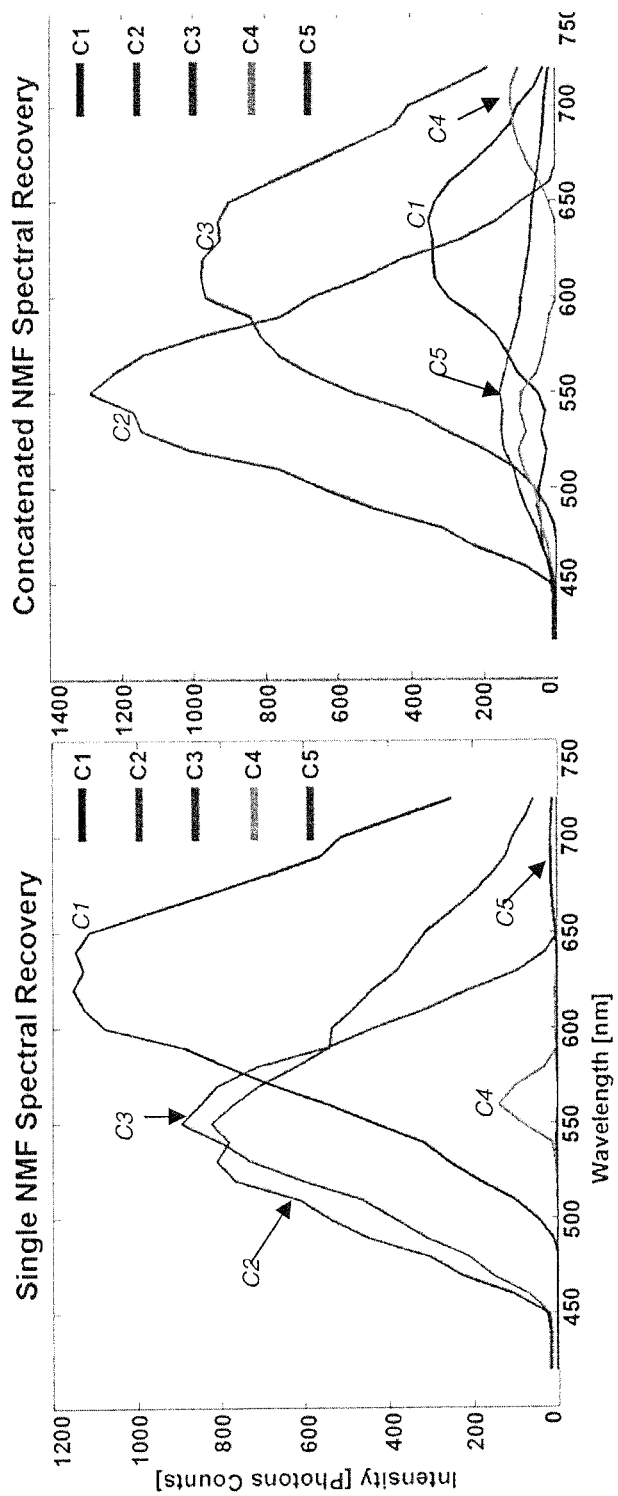
FIG. 5B illustrates examples no improvement in spectral recovery with concatenated NMF.

FIG. 5A shows examples of moderate improvement, and FIG. 5B shows examples of no improvement. In particular, FIG. 5A illustrates examples of moderate improvement in spectral recovery with concatenated NMF. As can be seen in FIG. 5A, jagged C2 and C3 are replaced by smoother C3 and C4, both significantly improved. The other signals are not improved. NTF improvement is graded moderate. FIG. 5B illustrates examples no improvement in spectral recovery with concatenated NMF. As can be seen in FIG. 5B, C5, almost degenerate, regains amplitude with NTF, but C4 changes from a single peak to two. Therefore the net improvement for FIG. 5B is graded as none.

Degenerate solutions, with less than 5 spectra recovered, were rare by either method. Interestingly, spectral recovery was most improved for the 480 nm excitations. Precisely, for 436 nm: 31/64 48% showed significant improvement; 20/64 31% showed moderate improvement; 5/64 7% showed no improvement, and 8 (14%) got worse. For 480 nm: 58/64 91% showed significant improvement; 4/64 6% showed moderate improvement; 2/64 3% showed no improvement, and none got worse. Remarkably, in almost all cases, the NTF system returned 4 candidate spectra that were similar to those in FIGS. 5A and 5B from all 60 tissue samples examined with two excitation wavelengths.

Example II

Bruch's Membrane Spectra Recovered from 3 Excitation Datasets

Figure 6:
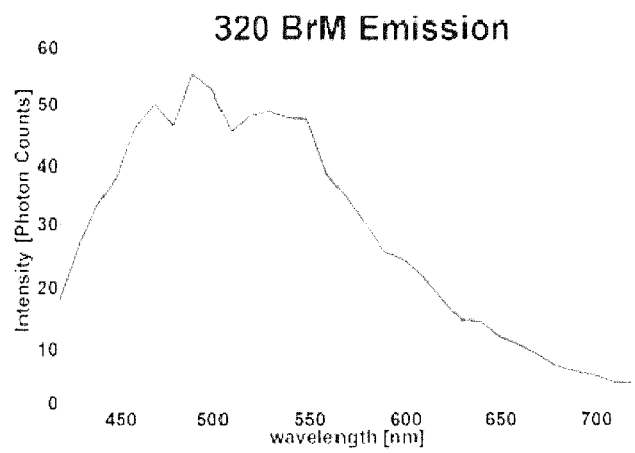
FIG. 6 illustrates an exemplary embodiment of BrM total emission spectra at excitations 320, 436 and 480 nm, respectively.
Figure 6:
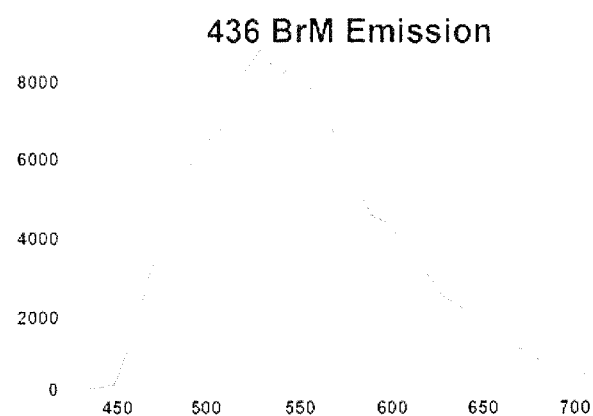
Figure 6:
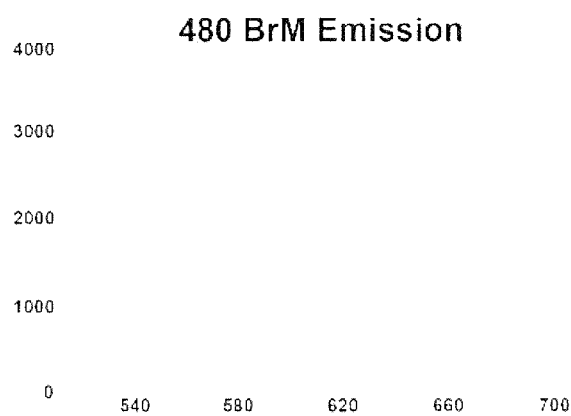

Example II focuses on signals from isolated BrM, excited with 3 different wavelengths: 436-460, 480-510, and a UV excitation at 320-340 nm, in 4 tissues. Thus, n=3 in the notation of the NTF section provided above. The main purpose was to show that the NTF method can be applied to a larger number of excitation datasets, with similar improvement in signal recovery. However, it is understood that the NTF method can be applied to a larger number of excitation datasets for a number of different type of tissue, in particular RPE. The NMF was initialized in each case with 3 Gaussians (k=3) that were fit to the BrM total emission spectrum at each excitation (FIG. 6, BrM emissions at 3 excitations, Gaussians not shown), analogous to that for the Gaussian fits to the RPE signal in the previous example. FIG. 6 illustrates an exemplary embodiment of BrM total emission spectra at excitations 320, 436 and 480 nm, respectively. Each signal was fit with 3 approximately evenly spaced Gaussians (not shown) in a manner similar to that in FIG. 3, discussed above. In each case, 3 abundant spectra were recovered. All nine Gaussians were then used to initialize the concatenated NMF. There was significant improvement in the quality of the recovered signals and the spatial specificity of the corresponding abundances in the concatenated solutions compared to the individual NMF solutions for each excitation dataset, particularly for the abundances of the UV excited signals (FIGS. 7A and 7B). Thus, the three abundance images (constrained to be identical for each excitation) showed significant spatial separation of the three recovered signals, a quality that was not present in the abundance images recovered separately.

Figure 7C:
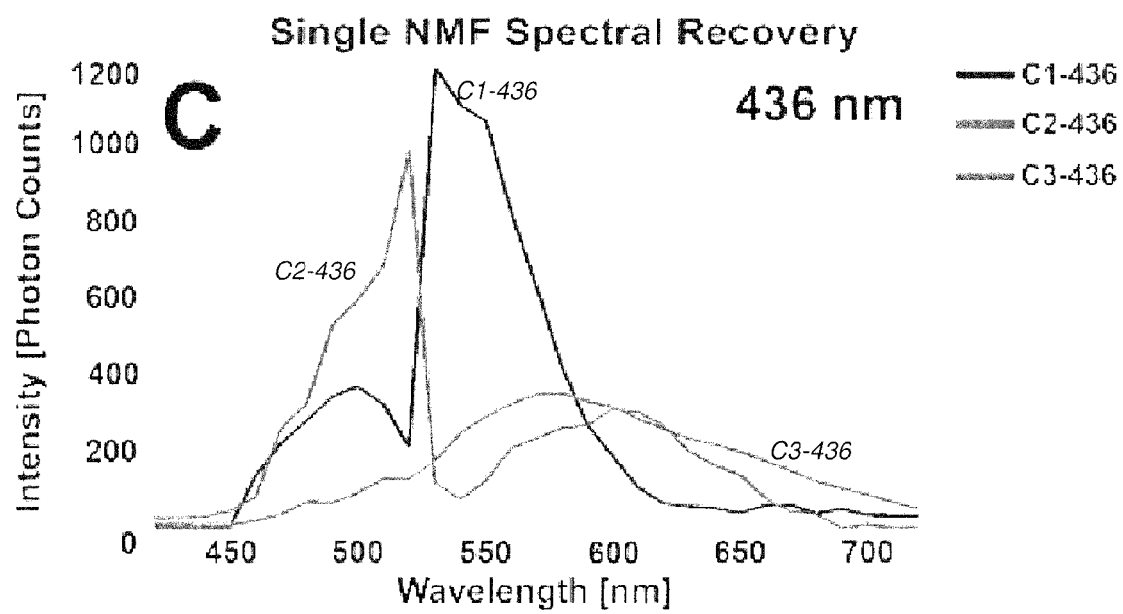
FIG. 7C illustrates an exemplary embodiment of spectral components generated using a single NMF spectral recovery method (e.g., decomposed from exemplary individual excitation datasets) obtained from an exemplary BrM spectrum received from 436 nm excitation.
Figure 7D:
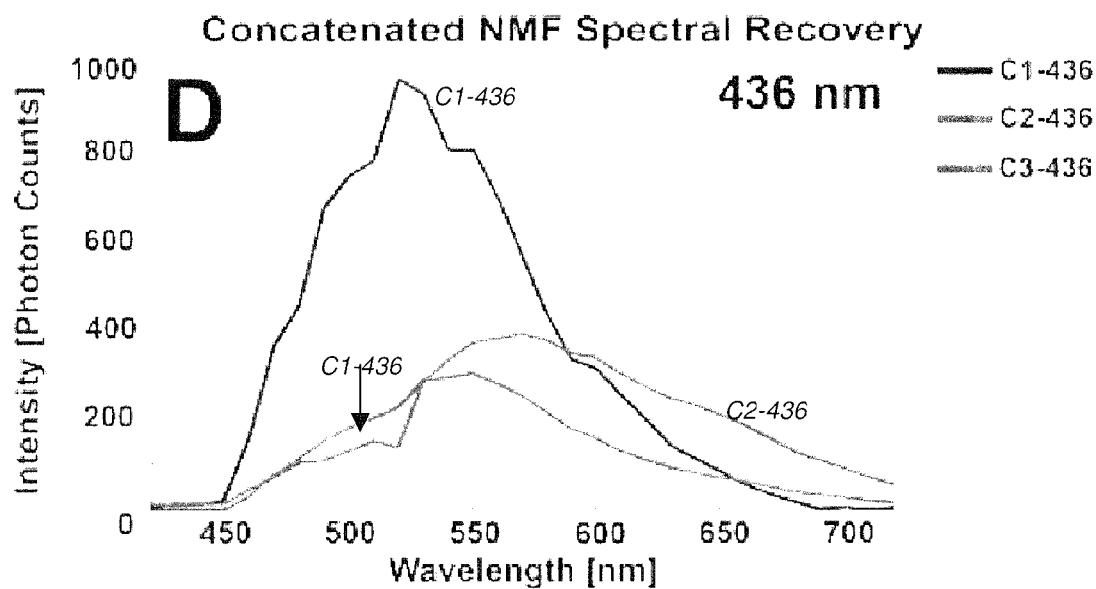
FIG. 7D illustrates an exemplary embodiment of spectral components generated using a concatenated NTF spectral recovery method (e.g., decomposed from simultaneous solution of three exemplary datasets) obtained from an exemplary RPE spectrum received from 436 nm excitation.
Figure 7E:
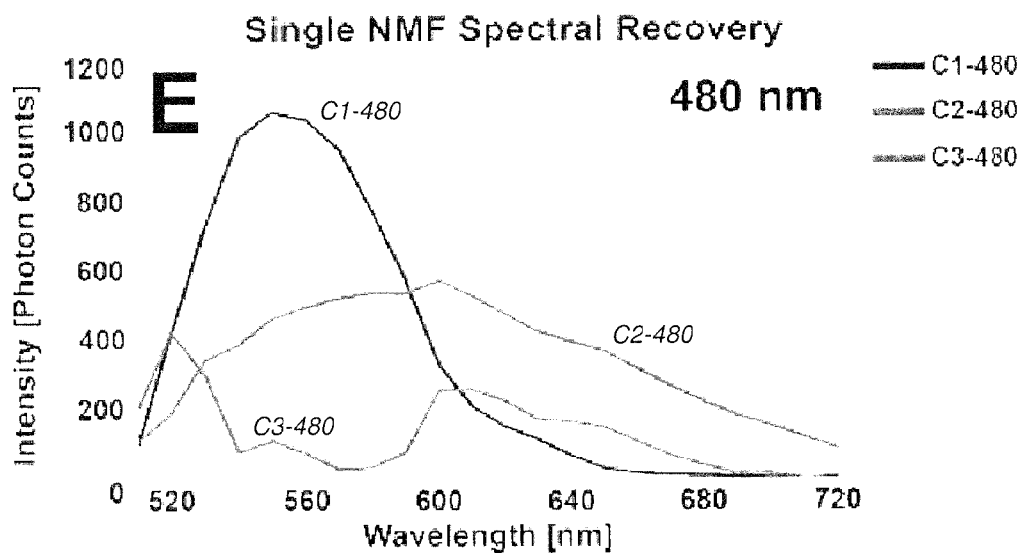
FIG. 7E illustrates an exemplary embodiment of spectral components generated using a single NMF spectral recovery method (e.g., decomposed from exemplary individual excitation datasets) obtained from an exemplary BrM spectrum received from 480 nm excitation.
Figure 7F:
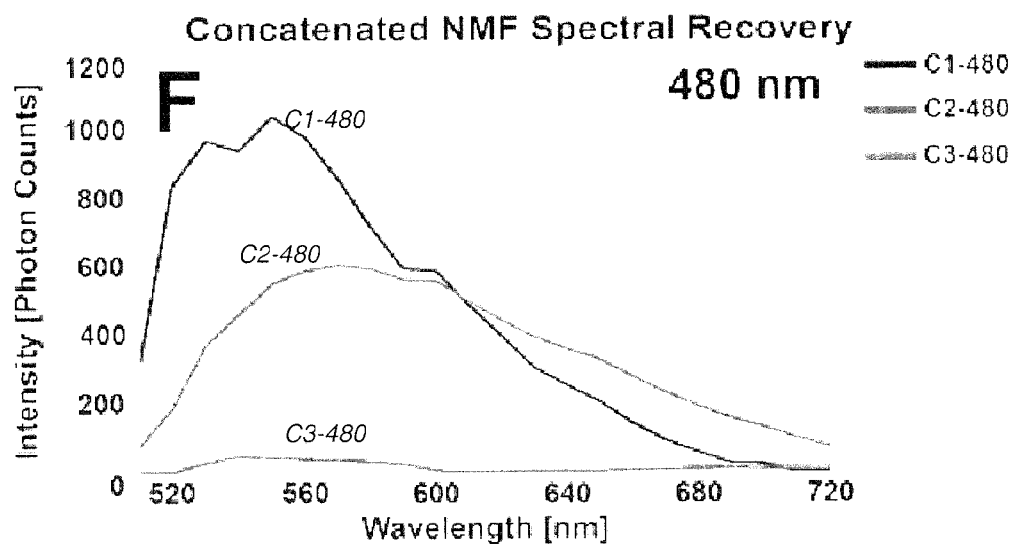
FIG. 7F illustrates an exemplary embodiment of spectral components generated using a concatenated NTF spectral recovery method (e.g., decomposed from simultaneous solution of three exemplary datasets) and two-dimensional abundance images of components of data obtained from an exemplary RPE spectrum received from 480 nm excitation.

The data shown in FIGS. 7A-7E suggest that these signals are more accurate representations of separate sources, with differing localizations, than the signals retrieved from the separate NMF solutions. The data shown in FIG. 7A-7E were obtained from isolated BrM, Perifovea of a 78-year-old female donor. FIGS. 7A and 7B show data for spectra recovered from 320 nm excitation. FIGS. 7C and 7D show data for spectra recovered from 436 nm excitation. FIGS. 7E and 7F show data for spectra recovered from 480 nm excitation. FIGS. 7A, 7C and 7B decomposed data of spectra from individual excitation datasets. FIGS. 7B, 7D and 7F decomposed data of spectra from NTF, simultaneous solution of all three concatenated excitation datasets. Three abundant signals are recovered with NMF decomposition of each individual excitation dataset, and with the concatenated solution. The corresponding abundance images are C1, C2 and C3 in each set. False coloring indicates the relative intensities of the signals. The panel lower right in of FIGS. 7A-7E is the composite RGB image from the total AF signal for that excitation.

FIGS. 7A and 7B show data representative of signal recovery with UV 320-340 nm excitation. The spectra are all noisy, but are broad, with dominant peaks. However, the signals C2 and C3 recovered by concatenation of datasets (i.e., NTF) are smoother than their counterparts recovered from NMF of the 320-340 nm excitation data alone. The abundance images all show the intercapillary pillars of BrM as a dotted pattern, but they are better defined and more spatially differentiated by NTF than the individual NMF.

FIGS. 7C and 7D show data representative of signal recovery information for 436-460 nm excitation. Emission spectra C1 and C2 by NMF have sharp peaks at about 530 nm, suggesting that a single signal has been split. They also each have subsidiary peaks, suggesting that additional components are present in each. Indeed, the abundances for C1 and C2 are quite similar, suggesting shared sources. C3 is more physiologic, with a single broad peak at around 575 nm, and an abundance different from those for C1 and C2. Note that the spectra recovered by NTF are dramatically improved. C1 has a broad peak at about 530 nm, replacing the split signals C1 and C2. The signal C2 is also markedly improved, with a small notch and otherwise a single, smooth peak.

FIGS. 7E and 7F show data representative of signal recovery with 480-510 nm excitation. By NMF, all signals have broad peaks and similar abundances, although C3 has an extra emission peak in the blue. By concatenated NMF, C2 now appears similar to the C2, albeit notched, from the 436 nm excitation, and C1 is red-shifted about 30 nm from its 436 nm counterpart, again with a similar contour. This suggests that there are common sources S1 and S2 for these paired signals, a conclusion not supported by the individual NMF results.

Although the above-described exemplary embodiments are described with respect to fluorescent imaging of fluorophors in an eye, those skilled in the art will understand that the methods and systems described herein may also be applicable to fluorescent imaging of any mixture of fluorophores in a biochemical system, including any type of tissue or biological source that provides autofluorescence, i.e., endogenous fluorescence, or that may be labelled with an exogenous fluorescent material or marker. For example an exogenous fluroescent may be imparted immunofluorescent labelled immunoglubulins. In one exemplary embodiment, the hyperspectral imaging device 10 as shown in FIG. 1A and method 100, in particular steps 120, 130 and 140 as shown in FIG. 1B may be applicable to any autofluorescent biochemical system, e.g., any suitable tissue or biologic source having autofluorescence. In particular, the autofluorescent biochemical system may provide hyperspectral AF emissions in response to excitation signals at one or more wavelengths; the data generated from the biochemical system may be analyzed by first identifying one or more Gaussian functions, wherein each Gaussian function is an initial approximation representative of a spectral component of the hyperspectral AF emissions, and applying NMF or NTF initialized with the one or more Gaussian functions to generate one or more component matrices, wherein each component matrix is an approximation representative of a spectral component of the biochemical system. Each spectral component may be compared to or calibrated against a fixed fluorescent reference material to quantify an amount, concentration and/or distribution fluorophors present in the biochemical system, e.g., any type of tissue or biological source emitting endogenous or exogenous fluorescence. For example, the exemplary methods described herein may be useful for quantifying an amount, concentration, or distribution of fluorophores in assessing neoplastic growth in epithelial tissue sites.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A method for generating an isolated autofluorescence image of lipofuscins endogenously generated in a retinal pigment epithelium (RPE) of an eye from composite autofluorescence detected from a plurality of fluorophors in the eye, wherein the plurality of fluorophors comprises the lipofuscins, the method comprising:
   obtaining, from a plurality of hyperspectral sensors, a first data matrix representative of a first electromagnetic emission spectrum from the plurality of fluorophors in response to an excitation signal;
   isolating, with a processor, a second data matrix from the first data matrix, the second data matrix being representative of a second electromagnetic emission spectrum from a retinal pigment epithelium (RPE) of the eye in response to the excitation signal;
   identifying, with the processor, one or more Gaussian functions, wherein each Gaussian function is an initial approximation representative of a spectral component of the second electromagnetic emission spectrum;
   analyzing, with the processor, the second data matrix using non-negative matrix factorization initialized with the one or more Gaussian functions to generate one or more component matrices, wherein each component matrix is a second approximation representative of the corresponding spectral component of the second electromagnetic emission spectrum; and
   generating, with the processor, an image of the lipofuscins corresponding to one of the component matrices, wherein the image approximately corresponds, in part, to a histological image of the eye;
   quantifying, with the processor, an intensity of one of the spectral components represented by the corresponding component matrix; and
   administering a treatment for a state of AMD disease progression corresponding to the quantified intensity.

2. The method of claim 1, wherein a composite of the one or more Gaussian functions approximates the second data matrix.

3. The method of claim 1, wherein the number of Gaussian functions corresponds to the number of peaks within the second electromagnetic emission spectrum.

4. A method for generating an isolated autofluorescence image of a component fluorophor from a plurality of fluorophors in an eye from composite autofluorescence detected from the fluorophors in the eye, comprising:
   obtaining, from a plurality of hyperspectral sensors, a first data cube representative of first electromagnetic emission spectra from the plurality of fluorophors in response to excitation signals having two or more different wavelengths;
   isolating, with a processor, a second data cube from the first data cube, the second data cube comprising a plurality of data matrices, each data matrix being representative of an individual emission spectrum from a retinal pigment epithelium (RPE) of the eye in response to the excitation signal at each of the different wavelengths;
   identifying, with the processor, one or more Gaussian functions for each data matrix, wherein each Gaussian function is an initial approximation representative of a spectral component of the corresponding individual emission spectrum;
   analyzing, with the processor, the second data cube using non-negative tensor factorization initialized with the one or more Gaussian functions for each data matrix to generate one or more component matrix functions, wherein the component matrix functions are concatenated across the plurality of data matrices such that each component matrix function is a common approximation representative of each corresponding spectral component shared across each individual emission spectrum; and
   generating, with the processor, an image from one of the plurality of fluorophors corresponding to one of the component matrix functions, wherein the image approximately corresponds, in part, to a histological image of the eye, wherein the fluorophors comprise lipofuscins endogenously generated in the RPE;
   quantifying, with the processor, an intensity of one of the spectral components represented by the corresponding component matrix; and
   administering a treatment for an eye disease corresponding to the quantified intensity.

5. The method of claim 4, wherein the excitation signals have three or more different wavelengths.

6. The method of claim 4, wherein a composite of the one or more Gaussian functions for each data matrix approximates the corresponding data matrix.

7. The method of claim 4, wherein the number of Gaussian functions for each data matrix corresponds to the number of peaks within each individual emission spectrum.

8. The method of claim 4, wherein the excitation signals are in 10 nm intervals between 420 nm to 720 nm.

* * * * *